United States Patent [19]

Rogers, Jr.

[11] 4,347,213

[45] Aug. 31, 1982

[54] METHOD OF FORMING CONTOURED CUSHION

[76] Inventor: John E. Rogers, Jr., 700 N. Valley St., Anaheim, Calif. 92801

[21] Appl. No.: 134,981

[22] Filed: Mar. 28, 1980

[51] Int. Cl.³ .............................................. B29D 9/04
[52] U.S. Cl. .................................... 264/510; 264/222; 264/320; 264/321; 264/511; 264/571; 264/DIG. 30; 264/DIG. 78
[58] Field of Search ............... 264/320, 222, 321, 223, 264/DIG. 30, 510, 511, 571, DIG. 78

[56] References Cited

U.S. PATENT DOCUMENTS 3,830,896 8/1974 Flicker et al. .............. 264/DIG. 30
3,905,376 9/1975 Johnson et al. ............ 264/DIG. 30

Primary Examiner—James R. Hall
Attorney, Agent, or Firm—William C. Babcock

[57] ABSTRACT

A method of making a contoured cushion removably disposed on a recess defining support, with the cushion contour conforming to the shape of the portion of a person's body resting on the cushion.

13 Claims, 12 Drawing Figures

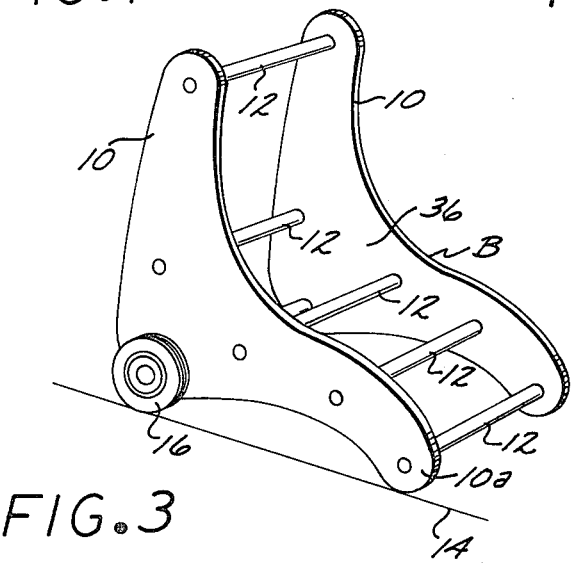
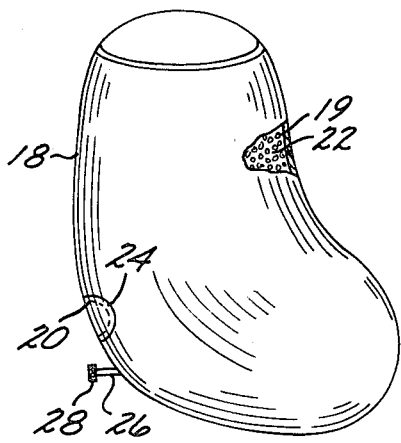
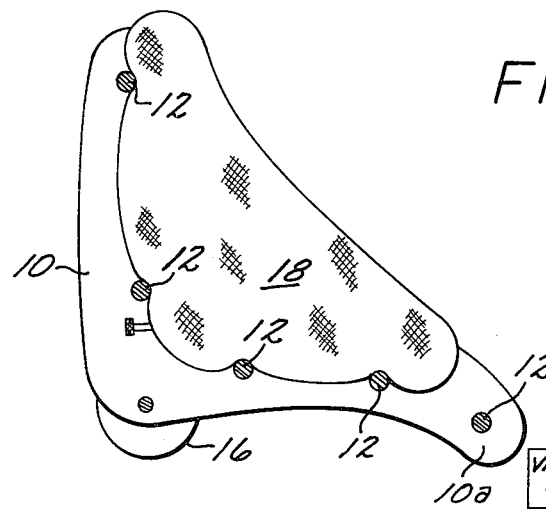
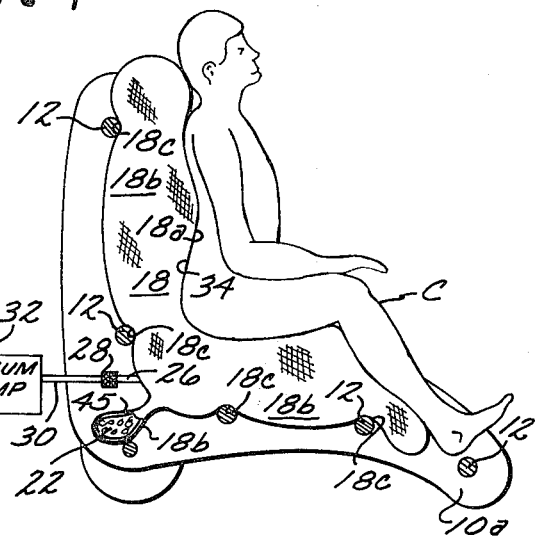
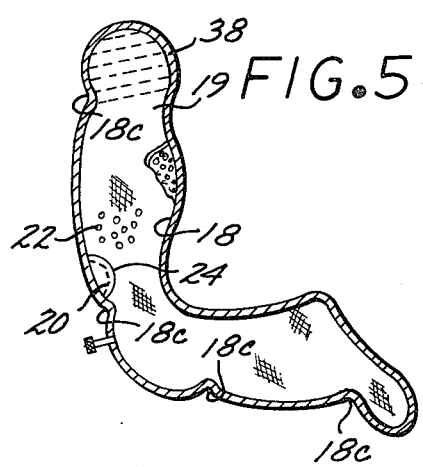
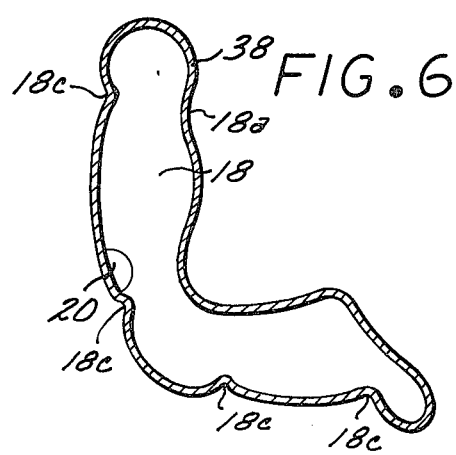

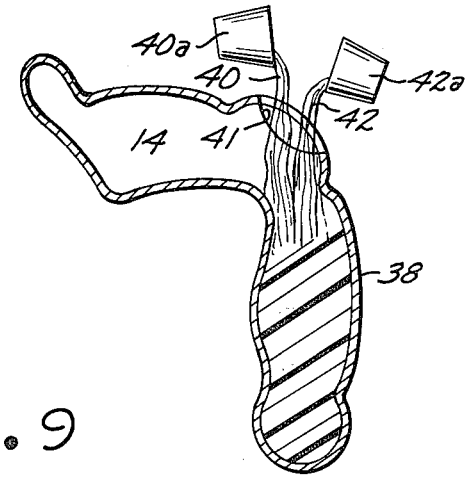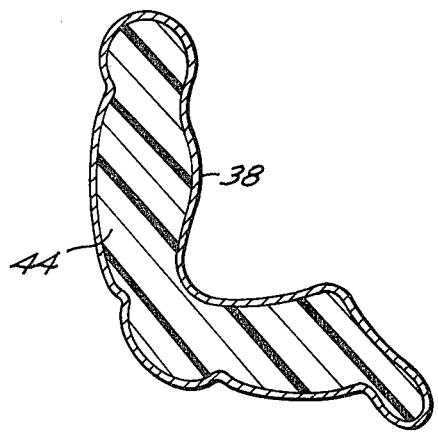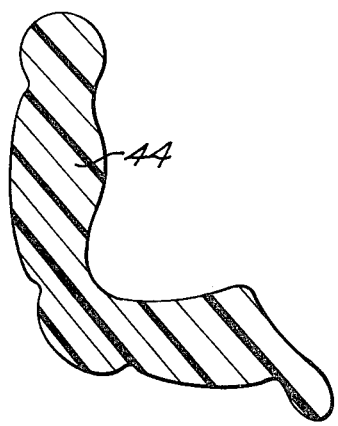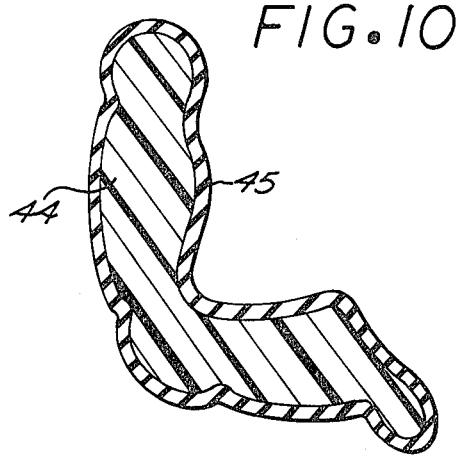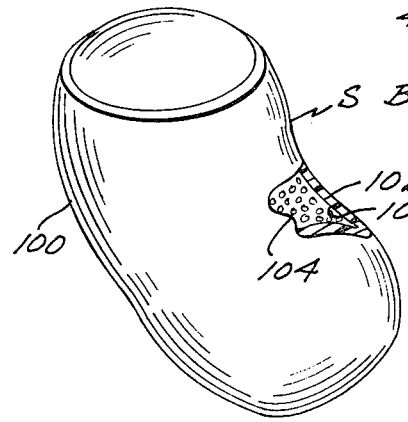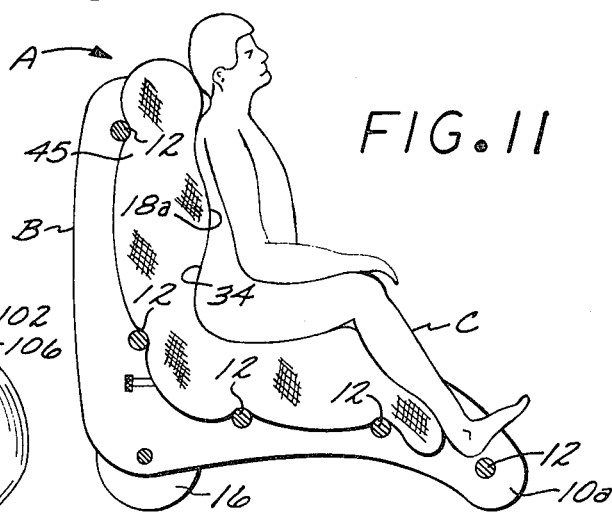

METHOD OF FORMING CONTOURED CUSHION

BACKGROUND OF THE INVENTION

1. Field of the Invention

Forming Contoured Cushion

2. Description of the Prior Art

In numerous situations, persons are either due to infirmities or their particular occupation, required to remain seated for prolonged periods of time. Examples of such persons are patients confined to wheelchairs and in institutional environments; drivers of various types of land and airborne vehicles; assembly line workers; office workers; radar and control operators and the like. The seats provided for such persons are normally mass produced and conformed to an average contour of a person, and as a result, a person in a sitting position in a mass produced chair has substantially his entire weight supported on a few localized pressure areas. If the person is an invalid or suffering from infirmaties wherein he must remain on the mass produced chair for prolonged periods of time, the body portion in contact with the chair may suffer a breakdown of tissues or damage to nerves.

In the past a support that will conform generally to the contour of a desired portion of a patients body, has been effected by covering that portion of the body with plaster of paris bandages and holding them in a functional position for a sufficient length of time to let the plaster of paris fit. The rigid plaster of paris is then removed from the patient's body and used as a form in which to pour a plaster of paris mixture, which mixture when set will be representative of the original portion of the patient's body. This plaster of paris form may be modified at the discretion of the fitter to a desired configuration. The solidified form now has plastic applied to the exterior surface thereof, with the plaster when it is polymerized conforming to the shape of the form, and also to the shape of a portion of the patient's body. Forming a support in the above-described manner requires a high degree of skill on the part of the fitter, and as a result there is no assurance that it will conform exactly to the contour of the patient and that there will not be pressure areas on the patient's body when he is sitting or supported therein.

An operational disadvantage of the prior method of providing a patient support that will conform exactly to the contour of a desired portion of its body is that the patient is put to considerable discomfort, and due to the high degree of skill required by the fitter there may be an error in design of the finished support. Also, the providing of a patient support by the prior art method above-described requires a substantial amount of time to effect, as well as being relatively expensive.

A major object of the present invention is to provide a method of forming a contoured cushion in which the method can be carried out by a person having a minimal skill in this regard, with the finished cushion capable of being delivered to the patients in a relatively short length of time, and the cost of cushion support being sufficiently low that it may be available to practically any patient that required such a support.

The method of forming the contoured cushion is carried out by providing a pliable bag that is sealed and partially filled with expanded styrofoam pellets or other suitable material that can be readily formed. The bag containing the soft pellets is placed under the desired support area of the patient's body and moved around appropriately so that the voids between the body and the structure on which the bag will be mounted, such as a wheel chair or the like, is filled. After the pellets have moved within the confines of the bag so that they conform approximately to the contour of the patient or user sitting on the bag or having a desired portion of his body in contact with the bag, a slight vacuum is applied to the interior of the bag. When the operator is assured that the pellets have moved relative to one another to cause the external surface of the bags to truly conform to the contour of the patient's body in contact therewith, the magnitude of the vacuum in the bag is increased, and the pellets interlock with one another to become a solid mass, such interlocking being of the type that occurs in a styrofoam cup or the like. The position of the patient's body resting on the bag containing the styrofoam pellets may now be readily evacuated, with X-rays being taken to check skeletal positioning. When the appropriate pressure or shear areas of the body are relieved by the pellets and the surface of the bag most adjacent thereto being in appropriate contact with the contoured portion of the patient's body, the invention is ready for the next step in the fabrication of the patient support.

At this intermediate step in the method of forming the contour conforming support, the operator has two choices in completing the method. In the first choice, the pellet containing bag that has been contoured to conform to the body of the patient, with a vacuum still applied to the interior thereof, has a build-up of plaster or other material applied to the exterior surface of the bag to minimize ridges, bumps and creases that may be formed therein. The build up is primarily for effecting a smooth external surface on the support that will conform to the contour of the patient that will use the same, and present portions of the patient's body being subjected to undue pressure. In other words, the body of the patient will be subjected to a minimum force, when all available areas of the body of the paitent is in full contact with the external surface of the contoured support. After the build up has been completed, the pellet containing bag may have a suitable release agent applied over its surface. The bag is then wrapped with bandages that are impregnated with plaster of paris or like material. When the plaster of paris is set, the vacuum is released, and the bag with the pellets is withdrawn from the rigid shell of plaster of paris or other material that is solidified. One technique is to cut a relatively small opening through the plaster of paris shell to permit the pellets to be discharged from the interior of the bags, leaving the bags as a liner. When it is elected to remove the bag and pellets, the plaster of paris rigid shell that serves as a mold has a suitable release agent applied to the interior surface thereof. The interior of the shell that serves as a mold is then filled with a light weight material such as polyurethane and a catalyst, with the polyurethane polymerizing to a rigid mass that completely fills the interior of the shell that serves as a mold. After the polyurethane has polymerized, and has become rigid, the external shell defined by the plaster of paris impregnated bandages is removed and the core of solidified polyurethane now defining the contour conforming support for a patient or other user. A suitable covering is placed over the entire external surface of the solidified core, which covering may be a film of rubber or other material such as resin fiberglass, or the like, and the contour conforming support is now complete and ready for delivery.

The second choice of completing the method includes utilizing the pellet containing bag with vacuum still applied thereto, and the external surface of the bags being smoothed with appropriate material then the whole rigidized by applying a polyester monomer with a catalyzing agent thereto, to form a rigid shell on the exterior surface of the contoured bag. After the rigidizing material has solidified, a suitable film of a resilient material, selected rubber or the like is applied thereto, which has sufficient friction to prevent the patient or user inadvertently sliding from the completed contour conforming support. This high friction surface may not be required where patients have reasonable body control and a more appropriate surface is selected. It will be apparent from the above description that the first and second choices in completing the method may both be carried out by inexperienced personnel, and with the end product namely the contour conforming support for a patient or user being the same. In the first choice in completing the method the mold could be fed to a central fabrication area for completion. However, this process takes longer, but it eliminates the need to have supplies available at the local facility and the pellets and bags may be reused if desired. Although the methods above have been described primarily relative to the total body support system for the patient or user, it will be obvious that it may be used equally well to hold any desired portions of the body in a relatively fixed position, and with the weight of either the whole or part of the body being distributed over a maximum area of the contour conforming support. For instance, the contour conforming support may be one that is utilized in supporting the trunk, arms, hands, seating, prostheses, and other orthotic uses. The contour conforming support as above described when being formed to conform to the contour of of the portions of the patient's body, is also shaped in the lower portion thereof to conform to a recessed portion in a mobile unit or a dolly, and the resulting combination serving as an inexpensive wheelchair for use in hospitals and other institutions in which the same is required either for permanent or temporary use by patients.

BRIEF DESCRIPTION OF THE DRAWINGS

FIG. 1 is a mobile unit or dolly of inexpensive construction that is utilized in removably supporting the contour conforming support for a patient or a user;

FIG. 2 is a perspective view of an enclosed pliable bag that is partially filled with flowable particled material such as soft styrofoam pellets, with the pellets being introduced through an opening that is covered with a patch, and the bag having a tubular member extending therethrough by which a partial vacuum may be formed on the interior of the bag;

FIG. 3 is a side elevational view of the dolly supporting the pliable bag shown in FIG. 2;

FIG. 4 is a side elevational view of a dolly, with the bag mounted thereon, and the patient or user sitting on the bag to cause the styrofoam pellets to conform to the contour of the portion of the patient's body in contact with the bag, when a vacuum is exerted on the interior of the bag;

FIG. 5 is a vertical cross-sectional view of the bag after being deformed to the contour of a patient or user, and removed from the dolly, with the contoured bag having a sequence of impregnated plaster of paris bandages applied to the external surface thereof which when the plaster of paris solidifies provides a hollow form or shell;

FIG. 6 is a vertical cross-sectional view of the contour conforming support with the patch removed from the opening therein to permit either all of the styrofoam pellets to discharge through the opening, or the pellets and resilient bag to be removed by being moved outwardly through the opening;

FIG. 7 is a vertical cross-sectional view of the contour conforming rigid form after the styrofoam pellets or styrofoam pellets and bags have been moved outwardly through the opening therein, and a polymerized monomer together with a catalyst being poured into the confines of the bag to polymerize to define a foamed resin core;

FIG. 8 is a vertical cross-sectional view of the contour deforming mold or shell after the latter has been filled with a foamed polymerized resin;

FIG. 9 is a vertical cross-sectional view that is the same as shown in FIG. 8 but after the plaster of paris or other rigid rising material has been cut or stripped therefrom;

FIG. 10 is the same vertical cross-sectional view of the contour conforming support as shown in FIG. 9 but after a layer or envelope of a resilient material that has a substantial coefficient of friction has been applied to the exterior surface of the core, and this resilient material preventing a user or patient inadvertently slipping from the contour conforming support;

FIG. 11 is a side elevational view of the completed contour conforming support mounted in the dolly shown in FIG. 1, and the dolley and contour conforming support serving to support a user in such a manner that substantially the entire contoured surface of the user that was initially employed in defining the contour on the support is fully supported on the dolly contour conforming support combination; and FIG. 12 is a perspective view of a pliable heavy walled bag at least partially filled with foam or beads that are impregnated with a polymerizable resin, which bag is adapted to conform to the portion of a patient's body that is in pressure contact therewith, and the bag after the resin has set remaining in the surface contour to which it was deformed by this pressure contact.

DESCRIPTION OF THE PREFERRED EMBODIMENTS

The contour conforming support A shown in FIG. 11 is preferably removably mounted on a mobile dolly B illustrated in both FIGS. 1 and 11. The support A is illustrated in FIG. 11 with a user of patient C resting thereon, with the portion of the support in contact with a selected part of the patient C conforming to the body contour of that part.

The dolly B is defined by two generally L-shaped side pieces 10 that are parallel and laterally spaced from one another. The side pieces 10 have a number of spaced parallel cross-pieces 12 extending therebetween. The side pieces 10 include forwardly disposed portions 10a that may removably contact a floor surface 14. Two wheels 16 are rotatably supported from the lower rear portions of the side pieces 10 as shown in FIG. 1.

An enclosed pliable bag 18 is provided that may be formed from a suitable commercially available plastic of which a number are available, such as polyethylene or the like.

The bag 18 has an opening 20 therein, preferably located in the lower rearward portion thereof as viewed in FIG. 2. Particles of a flowable soft material 22, such as soft styrofoam pellets, are introduced into the bag 18 through the opening, with a patch 24 then being applied to the bag to cover the opening. The bag 18 has a first tube 26 extending outwardly from the lower rearward portion of the bag, which tube is in communication with the interior 19 of bag 18 in which the particles 22 are disposed. First tube 26 on the free end terminates in a coupling 28 to which a second tube 30 may be removably connected. The second tube 30 is connected to a power driven vacuum pump 32.

The first step in forming the contour conforming support A for a patient C as shown in FIG. 11, is to place the particle containing bag 18 on the dolly B as shown in FIG. 3. The patient C is now seated on the bag 18 and is moved laterally and vertically thereon to cause the particles 22 to flow relative to one another and the bag 18 having a surface portion 18a thereof conform to the contour 34 of the portion of the patient's body in contact with the bag.

The weight of the patient C sitting on the bag 18 forces the lower portion of the particle filled bag downwardly and rearwardly to contact the cross pieces 12 and laterally against the side pieces 10. Thus, not only is the particle filled bag 18 deformed to conform to the body contour 34 of the patient C in pressure contact with the bag, but also the bag being deformed to provide a portion 18b that removably fits within the space 36 between the side pieces 10.

The vacuum pump 32 is now actuated to provide a slight vacuum within the interior 19 with the patient C moved laterally and vertically within a limited range to assure maximum flow of the particles 22 relative to one another and assure that the surface 18a of the bag conforms to the contour 34 of patient C. The magnitude of the vacuum is now increased, and this increase in cooperation with the weight of the patient C causing the soft styrofoam particles to merge with one another, such as occurs in the particles that define a styrofoam cup.

The patient C is now caused to arise from the bag 18, which bag is now removed from the dolly B while the vacuum is maintained on the interior 19 thereof. The deformed bag 18 is now wrapped and enveloped in bandages soaked in a plaster of paris solution or other rigidizing material. After the plaster of paris or rigidizing material has set, the vacuum is discontinued, and the rigid shell 38 resulting from this operation constituting a form that closely conforms to the contour 34 of the patient C as shown in FIGS. 4, 5 and 6. Bumps and ridges in the patient contour conforming shell 38 may be smoothed out by a thin layer of plaster of paris being applied thereto to mask the bumps and ridges.

At this intermediate stage in the method the operator has first and second choices as to how to continue the method to completion. In the first choice an opening 41 is cut through the rigid shell 38 and bag 18 to communicate with the interior 19. The styrofoam particles 22 which may be in the form of beads are removed from the interior 19 through opening 41.

After the pellets 22 and bag 18 have been removed from the interior 19 of shell 38 the shell is disposed as shown in FIG. 7, with a polymerizable monomer 40 such as polyurethane being poured into the interior through the opening 41 in the shell together with a catalyst 42 from containers 40a and 42a. The monomer 40 and catalyst 42 react in the interior 19 to form a foamed resin core 44 of a desired degree of hardness. The hardness of the foamed resin core 44 is controlled by the amount of catalyst 42 used. Prior to pouring the monomer 40 and catalyst 42 into interior 19, the inner surface of shell 38 is coated with a conventional release agent (not shown). The shell 38 is now cut into sections and separated from the core 44 of foamed resin. The core 44 now has a resilient film 46 of rubber or the like applied thereto as shown in FIG. 6, which film has a substantial coefficient of friction to prevent the patient C inadvertently sliding therefrom. After coating with the film 46 the contour conforming support is complete and may be removably mounted in the dolly B as shown in FIG. 11.

In the contouring of the particle holding bag 18 it may be desired to provide a downwardly disposed extension 18d that defines a confined space 45 as shown in FIG. 4 into which excess particles 22 may be forced due to the weight of the patient C. The excess particles 22 in confined space 45 are separated from the balance of the pellets in bag 18 by severing the extension 18d from the latter prior to wrapping the contoured bag with plaster of paris impregnated bandages that upon solidification define shell 38.

The second choice is continuing the method from the intermediate step previously identified is to envelop the contour conforming particle containing bag 18 as shown in FIG. 4 with a rigidizing material such as any one of the commercially available polymerizable resins, polyurethane or the like, while maintaining a vacuum on the interior 19 of the bag. The polymerizable resin where it sets defines a resilient contour conforming shell 38 that has the same configuration as the shell defined by plaster of paris. After the polymerizable resin has set the extension 18b is served from bag 18. The second choice in continuing the method from the intermediate step may be accomplished faster than the first choice and can be carried out by inexperienced personnel. After thhe rigidizing material above referred to has set, film of the resilient material 45 is applied thereto.

An alternate method of forming a contour conforming support S for the patient C is to utilize a pliable bag 100 as shown in FIG. 12 that is formed from a relatively thick sheet material 102, such as the polymerized resin used in forming skin diving suits. Due to the thickness and pliability of such sheet material 102, it has a minimum tendency to wrinkle on the exterior surface thereof when the bag 100 is deformed.

The bag 100 is at least partially filled with styrafoam beads 104 that are intimately mixed with a polymerizable resin 106, and the bag then being palced on the dolly in the same manner as described in connection with bag 18. The patient C is now seated on the dolly supported bag 100, and moved laterally and vertically relative to the bag to cause the latter to conform to the portion of the patient's body in pressure contact therewith. After the polymerizable resin 106 has polymerized it will bond the beads 104 into the shape it has been deformed, as well as bonding the interior of sheet 102 thereto. The bag 100 may be provided with a vent (not shown) to permit escape of gases that may be generated as the polymerizable resin polymerizes. Upon completion of the polymerization of the polymerizable resin the support S is completed. The bag 100 as may be seen in FIG. 12 is elongate in shape and of such size as to be contacted by the back, buttocks and rear portion of the legs of the patient C in the same manner as shown in FIG. 11. However, the support S is not limited to this use. The support S if desired may be used to conform only to a portion of the body of the patient C, such as an arm or leg, and in this case the support S need not be held in the dolly B. In other words the support S, is adapted to form all or a portion of a cast for an arm or leg of the patient C. It will be apparent that the support S may be formed as two abutting halves that completely envelop an arm or leg of a patient C, and held in this abutting position by encircling bands (not shown) or other conventional holding means.

The methods of forming the contour conforming supports A and S have been previously described in detail as well as the use of the supports in the mobile unit B or apart therefrom if desired. The lower and rearward portions of the support A are adapted to be removably disposed between side pieces 10 to rest on cross pieces 12 of the dolly B. Due to the support A having been partially formed in contact with cross pieces 12, the completed support A has a number of spaced elongate recesses 18c therein that removably engage the cross pieces to prevent the support A inadvertently being displaced from the dolly B. The contour conforming support A has been illustrated as being in contact with substantial portions of the back, buttocks and the legs of the patient C, but may be used equally well in affording full contour area support to any desired portion of the human body.

What is claimed is:

1. A method of making a contoured cushion removably disposed on a recess defining support, said cushion contours conforming to the shape of the portion of a person's body resting on said cushion, comprising:
   a. providing a pliable closed bag that is substantially filled with a plurality of particles that tend to flow relative to one another when subjected to pressure;
   b. disposing said bag in said recess defining support;
   c. positioning said person on said bag when the latter is disposed in said recess defining support and subsequently causing said person to move relative to said recess defining support, with the weight of said person causing said particles in said bag to flow relative to one another for a first portion of said bag in contact with said body of said person to conform to the contour thereof, and a second portion of said bag in said recess defining support to assume the shape thereof;
   d. applying a partial vacuum to the interior of said bag to hold the same in the configuration to which it has been deformed by the weight of said person being supported thereon;
   e. removing said person from said bag;
   f. removing said bag from said recess defining support while maintaining said partial vacuum on the interior of said bag;
   g. applying a fluid solidifiable material to the exterior of said bag while maintaining said partial vacuum thereon to substantially envelop said bag, said material being of a type that solidifies upon standing for a period of time and said material after solidifying providing a shell that tends to hold said bag in the shape to which it has been deformed;
   h. releasing said partial vacuum after said material has solidified; and
   i. disposing said bag on said recess defining support to serve as said cushion for said person to rest thereon, and said cushion conforming to the contour of the portion of the body of said person in contact therewith.

2. The method as defined in claim 1 in which said recess defining support has wheels mounted thereon, with said recess defining support serving the dual function of a mold in the forming of said contoured cushion, and as a vehicle to permit said person to be moved from place to place after said contoured cushion has been completed and disposed in said recess defining support with said person resting thereon.

3. The method as defined in claim 1 which includes the further step of:
   h. applying a film of a resilient material to said cushion after said solidifiable fluid has solidified, said resilient material having a high coefficient of friction and tending to prevent said person inadvertently sliding from said cushion when the latter is mounted in said support.

4. A method as defined in claim 1 in which said particles are styrofoam beads that tend to bond to one another when subjected to pressure and to said partial vacuum.

5. A method as defined in claim 1 in which said particles are any suitable particulate capable of conforming to an undulating surface such as that of a persons body.

6. A method of making a contoured cushion removably disposed on a recess defining support, said cushion contours conforming to the shape of the portion of a person's body resting on said cushion, comprising:
   a. providing a pliable closed bag that is substantially filled with a plurality of particles that tend to flow relative to one another when subjected to pressure;
   b. disposing said bag in said recess defining support;
   c. positioning said defining support person's body on said bag when the latter is disposed in said recess defining support and subsequently moving said person's body relative to said recess defining support, with the weight of said person's body and said movement causing said particles in said bag to flow relative to one another for a first portion of said bag in contact with said person's body conforming to the contour thereof, and a second portion of said bag in said recess defining support assuming the shape thereof;
   d. applying a partial vacuum to the interior of said bag to hold said bag in the configuration to which it has been deformed by the weight of said person's body being supported thereon;
   e. removing said bag that has been deformed from said recess defining support while maintaining said partial vacuum thereon after said person has arisen from said bag;
   f. applying a layer of fluid solidifiable material to the exterior surface of said bag while maintaining said vacuum thereon to substantially envelop said bag;
   g. allowing said fluid to solidify to form a rigid shell;
   h. releasing said vacuum;
   i. cutting an opening in said shell and bag;
   j. removing said bag and substantially all of said particles through said opening;
   k. pouring a liquid polymerizable resin together with a catalyst into the interior of said shell;
   l. allowing said resin to polymerize to define a non-flowable core;
   m. cutting said shell from said core;
   n. enveloping said core in a film of resilient material; and
   o. disposing said resilient film enveloped core in said recess defining support to provide said contoured cushion for said person's body to rest thereon.

7. The method as defined in claim 6 in which said particles are beads and said core is resilient.

8. The method as defined in claim 6 in which said recess defining support has wheels mounted thereon, with said recess defining support serving the dual function of a mold in the forming of said contoured cushion, and as a vehicle to permit the person supported on said contoured cushion to be moved from place-to-place after said cushion has been completed and disposed in said recess defining support.

9. A contour conforming cushion made in accordance with the method of claim 1.

10. A contour conforming cushion made in accordance with the method of claim 5.

11. A method of making a contoured cushion removably disposed on a recess defining support, said cushion contours conforming to the shape of the portion of a person's body resting on said cushion, comprising:
 a. providing a pliable closed bag that is substantially filled with a plurality of particles that tend to flow relative to one another when subjected to pressure;
 b. disposing said bag in said recess defining support;
 c. positioning said portion of said person's body on said bag when the latter is disposed in said recess defining support and subsequently moving said portion of said person's body relative to said recess defining support, with the weight of said portion of said person's body and said movement causing said particles in said bag to flow relative to one another for a first portion of said bag in contact with said portion of said person's body to conform to the contour thereof, and a second portion of said bag in said recess defining support to assume the shape thereof;
 d. applying a partial vacuum to the interior of said bag to hold the same in the configuration to which it has been deformed by the weight of said portion of said person's body being supported thereon;
 e. removing said bag from said recess defining support while maintaining said partial vacuum thereon after said person has risen from said bag;
 f. applying a film of a polymerizable resin to the exterior of said bag while maintaining said vacuum on the interior thereof;
 g. polymerizing said resin to provide a resilient envelope in which said deformed bag is disposed;
 h. releasing said vacuum; and
 i. returning said bag within said resilient envelope to said recess defining support to provide said contoured cushion for supporting said portion of a person's body.

12. A method of making a contoured cushion removably disposed on a recess defining support, said cushion contours conforming to the shape of the portion of a person's body resting on said cushion, comprising:
 a. providing a pliable closed bag that is formed from a polymerized resin sheet of sufficient thickness that it will not wrinkle substantially when said bag is deformed;
 b. at least partially filling said bag with a flowable polymerizable resin and a plurality of resilient particles intermixed therewith;
 c. disposing said bag in said recess defining support;
 d. positioning said portion of said person's body on said bag when the latter is disposed in said recess defining support and subsequently moving said person relative to said recess defining support, with the weight of said portion of said person's body and said movement causing said particles in said bag to flow relative to one another for a first portion of said bag in contact with said portion of said person's body to conform to the contour thereof, and a second portion of said bag in said recess defining support to assume the shape thereof;
 e. causing said polymerizable resin to polymerize to bond said particles to one another and to the interior of said bag, with said contoured cushion for said portion of said person's body being complete for supporting the latter when said resin has polymerized; and
 f. removing said person from said bag after said resin has polymerized.

13. The method as defined in claim 12 in which said particles are resistant.

* * * * *